United States Patent [19]

Hou et al.

[11] 4,368,267

[45] Jan. 11, 1983

[54] EPOXIDATION OF LOWER α-OLEFINS

[75] Inventors: Ching-Tsang Hou; Ramesh N. Patel, both of Edison, N.J.; Allen I. Laskin, New York, N.Y.

[73] Assignee: Exxon Research and Engineering Co., Florham Park, N.J.

[21] Appl. No.: 119,096

[22] Filed: Feb. 6, 1980

Related U.S. Application Data

[63] Continuation-in-part of Ser. No. 896,467, Apr. 14, 1978, abandoned, and Ser. No. 21,227, Mar. 16, 1979, abandoned, and Ser. No. 24,262, Mar. 27, 1979, abandoned.

[51] Int. Cl.$^3$ ............... C12P 17/02; C12N 11/02; C12N 1/28; C12N 1/30
[52] U.S. Cl. ............... 435/123; 435/177; 435/249; 435/250; 435/822; 435/858
[58] Field of Search ............... 435/123, 177, 249, 250, 435/822, 858

[56] References Cited

U.S. PATENT DOCUMENTS

| | | | |
|---|---|---|---|
| 3,510,401 | 5/1970 | Wegner | 435/822 X |
| 3,639,210 | 2/1972 | Tanaka et al. | 435/250 X |
| 3,897,308 | 7/1975 | Li et al. | 435/177 |
| 4,106,986 | 8/1978 | Suzuki et al. | 435/123 |

FOREIGN PATENT DOCUMENTS

| | | |
|---|---|---|
| 54-17184 | 2/1979 | Japan . |
| 2788677 | 7/1977 | United Kingdom . |
| 2788677 | 5/1978 | United Kingdom . |
| 2024205 | 1/1980 | United Kingdom . |

OTHER PUBLICATIONS

Cerniglia et al., "Microbial Oxidation & Assimilation of Propylene" Applied & Environmental Microbiology, Dec. 1976, pp. 764-768.
Nesterov "Activity of $CH_4$ Oxidizing Bacteria in the Absorbed State" Chemical Abstracts, vol. 84, No. 5 (1976) Abstract No. 27940c.
Colby et al., "Soluble $CH_4$ Mono-Oxygenase of Methylococcus Capsulatus" Biochem. J., vol. 165 (1977), pp. 395-402.
van der Linden et al., "Induction of Alkane Oxidizing & α-Olefin Epoxidizing Enzymes by a Nonhydrocarbon in a Pseudomonas" Chem. Abst., vol. 67 (1967), Abst. No. 106124s.

*Primary Examiner*—R. B. Penland
*Attorney, Agent, or Firm*—Albert P. Halluin; Janet E. Hasak

[57] ABSTRACT

A process is disclosed for the epoxidation of lower α-olefins dienes or vinyl aromatic compounds by contacting said compounds, under aerobic conditions in the presence of microorganisms, genetically engineered organisms thereof or enzyme preparations derived from said microorganisms. The microorganisms, genetically engineered organisms, or enzyme preparations derived therefrom are preferably those microorganisms which are known as methylotrophs particularly those which have previously grown under aerobic conditions in a nutrient medium containing methane.

42 Claims, No Drawings

EPOXIDATION OF LOWER α-OLEFINS

CROSS REFERENCE TO RELATED APPLICATIONS

This application is a continuation-in-part of copending application Ser. Nos. 896,467, filed Apr. 14, 1978, now abandoned; 21,227, filed Mar. 16, 1979; and 24,262, filed Mar. 27, 1979, now abandoned. This application is related to U.S. application Ser. No. 896,476, filed Apr. 14, 1978, now abandoned.

FIELD OF THE INVENTION

The present invention relates to the conversion of lower α-olefins, lower branched olefins, vinyl aromatic compounds and dienes to epoxides. More particularly it relates to the formation of propylene oxide from propylene and streams containing the same, through the action of oxygen and methylotrophic microorganisms or enzyme preparations derived therefrom.

BACKGROUND OF THE INVENTION

Epoxides have become extremely valuable products due to their ability to undergo a plurality of chemical reactions such as addition with the active hydrogen atoms of nucleophilic reagents (e.g., ammonia, organic acids, alcohols, water, etc.). The products of epoxidation (i.e., 1,2-epoxides, also known as α-epoxides and oxirane compounds) have also enjoyed industrial importance because of their ability to polymerize under thermal, ionic, and free radical catalysis to form epoxy homopolymers and copolymers. Ethylene oxide and propylene oxide constitute the two most important commercial epoxides. A widely utilized process is the silver-catalyzed "direct oxidation" process of Lefort (U.S. Pat. No. 1,998,878 (1935) and Reissue Pat. Nos. 20,370 and 22,241).

DESCRIPTION OF THE PRIOR ART

In recent years there have been several publications relating to the microbiological oxidation of hydrocarbons including the epoxidation of α-olefins. These publications include:

Ishikura and Foster, *Nature*, 192, 892–893 (1961) "Incorporation of Molecular Oxygen During Microbial Utilization of Olefins";

van der Linden, *Biochim. Biophys. Acta*, 77, 157–159 (1963) "Epoxidation of α-olefins by Heptane-Grown Pseudomonas Cells";

Huybregtse and van der Linden, *Antonie van Leeuwenhoek*, 30, 185–196 (1964) "The Oxidation of α-olefins by a Pseudomonas-Reactions Involving the Double Bond";

van der Linden and Huybregtse, *Antonie van Leeuwenhoek*, 33 (4), 381–385 (1967) "Induction of Alkane-Oxidizing and α-Olefin-Epoxidizing Enzymes by a Nonhydrocarbon in a Pseudomonas"; and Cerniglia, Blevins and Perry, *Applied and Environmental Microbiology*, 32 (6) 764–768 (1976) "Microbial Oxidation and Assimilation of Propylene".

In these publications where the epoxidation of α-olefins is involved, it is shown that certain microorganisms which have been grown on alkanes will epoxidize 1-octene.

In Dutch Pat. No. 291,163 to Shell International Research Corp. Inc. (laid open for inspection June 25, 1965) there is disclosed a process for preparing 1,2-epoxides by contacting α-olefins with oxygen and microorganisms capable of growing on a hydrocarbon and assimilating carbon from it. This patent teaches that the microorganism is preferably grown on a hydrocarbon having substantially the same number of carbon atoms as the α-olefin that is subjected to epoxidation. While the general description in the patent includes α-olefins having from 2 to 30 carbon atoms, the only example in the patent shows the epoxidation of 1-octene in the presence of air and *Pseudomonas aeruginosa* (strain 473) which had been grown on n-heptane.

In the paper by DeBont and Albers (*Antonie van Leeuwenhoek*, 42 (1–2) 73–80 (1976) "Microbial Metabolism of Ethylene") it is disclosed that the ethylene-oxidizing strain (E 20) was grown on different carbon sources to obtain information on the metabolism of ethylene. It is disclosed in this paper that ethylene oxide is a product of ethylene catabolism and the bacterium was also able to grow on the epoxide.

Leadbetter and Foster (*Arch. Microbiology*, 30, 91–118 (1958) "Studies on Some Methane-Utilizing Bacteria") reported that methane-grown *Pseudomonas methanica* oxidized methanol, ethanol, n-propanol, n-butanol and n-pentanol stoichiometrically to the corresponding carboxylic acids but isopropanol, tertiary butyl alcohol and 1-decanol were not oxidized by this bacterium.

DeBont and Mulder (*J. Gen. Microbiology*, 83, 113–121 (1974) "Nitrogen Fixation and Co-Oxidation of Ethylene by a Methane-Utilizing Bacterium") reported that their methane-oxidizing strain 41 (presumably a Methylosinus) co-oxidized ethylene in addition to fixing nitrogen when this bacterium was grown in the presence of methane and acetylene. They did not indicate what oxidation product was formed by the oxidation of ethylene. In a more recent paper, however, (*Annals Applied Biology*, 81, 119–121 (1975) "Oxidation of Ethylene by Bacteria") DeBont speculated that ethylene oxide may be the microbiological oxidation product of ethylene in this microbiological oxidation. Dalton and Whittenbury (*Arch. Microbiol.*, 109, 147–151 (1976)) reported that in their electrode experiments ethylene was very slowly oxidized by suspensions of *M. capsulatus*. Dalton and Whittenbury stated at page 149: "It seems extremely unlikely that its oxidation by the cell would account for its disappearance by nitrogen-fixing methane oxidizing cultures as suggested by DeBont and Mulder (1974)".

Whittenbury, Dalton, Eccleston and Reed (Microbial Growth on $C_1$ Compounds: Proceedings of the International Symposium on Microbial Growth on $C_1$ Compounds, Society of Fermentation Technology, pp. 1–11 (1975) "The Different Types of Methane Oxidizing Bacteria and Some of Their More Unusual Properties") reported that methane-oxidizing bacteria possess the interesting feature of having the ability to oxidize, but not to utilize substrates, e.g., they will not grow on ethane but will oxidize it if they are growing on methane or if previously grown on methane.

DeBont (*Antonie van Leeuwenhoek*, 42, 59–71 (1976)) reported that ethylene was oxidized by certain gram-positive bacteria believed to belong to the genus Mycobacterium. DeBont reported that his isolated strains did not grow in the presence of methane and deduced that these bacteria located in the soil were not methane-oxidizing bacteria. DeBont and Albers (*Antonie van Leeuwenhoek*, 42, 73–80 (1976)) theorized that the oxidation product of the ethylene-oxidizing strains of DeBont (1976) was ethylene oxide.

Hutchinson, Whittenbury and Dalton (*J. Theor. Biol.*, 58, 325–335 (1976) "A Possible Role of Free Radicals in the Oxidation of Methane by *Methyloccus capsulatus*") and Colby and Dalton (*J. Biochem.*, 157, 495–597 (1976) "Some Properties of a Soluble Methane Mono-Oxygenase from *Methylococcus capsulatus* Strain Bath") reported that ethylene is oxidized by the soluble methane mono-oxygenase derived from *Methylococcus capsulatus* Strain Bath. The latter investigators reported that the "particulate membrane preparations" of *Methylococcus capsulatus* Strain Bath did not have methane-oxygenase activity as determined by the bromomethane disappearance test.

May, Schwartz, Abbott and Zaborsky (*Biochimica et Biophysia, Acta*, 403, 245–255 (1975) "Structural Effects on the Reactivity of Substrates and Inhibitors in the Epoxidation System of *Pseudomonas oleovorans*") reported that it is known that the enzyme system of *Pseudomonas oleovorans* catalyzes the epoxidation of terminal olefins in addition to the previously known methyl group hydroxylation of alkanes and fatty acids. These investigators found that this enzymatic epoxidation reaction exhibits a substrate specificity far different from that expected on the basis of chemical reactivity in non-enzymatic epoxidation reactions. These investigators found that for this enzyme system, when the carbon length is decreased below $C_8$ the epoxidation rate rapidly decreases whereas the hydroxylation rate increases. Their data show that propylene and 1-butene are hydroxylated to the corresponding unsaturated alcohols, but not epoxidated by this enzyme system. Their evidence is an illustration of the high degree of specificity and unpredictability of the oxidative ability of microorganisms.

On the basis of $^{18}O$ incorporation from $^{18}O_2$ into the cellular constituents of *Pseudomonas methanica* Leadbetter and Foster (*Nature*, 184: 1428–1429 (1959) "Incorporation of Molecular Oxygen in Bacterial Cells Utilizing Hydrocarbons For Growth") suggested that the initial oxidative attack on methane involves an oxygenase. Higgins and Quayle (*J. Biochem.*, 118:201–208 (1970) "Oxygenation of Methane by Methane-Grown *Pseudomonas methanica* and *Methanomonas methanooxidans*") isolated $CH_3^{18}OH$ as the product of methane oxidation when suspensions of *Pseudomonas methanica* or *Methanomonas methanooxidans* were allowed to oxidize methane in $^{18}O_2$-enriched atmospheres. The subsequent observation of methane-stimulated NADH oxidation catalyzed by extracts of *Methylococcus capsulatus* by Ribbons (*J. Bacteriol.*, 122:1351–1363 (1975) "Oxidation of $C_1$-Compounds by Particulate Fractions From *Methylococcus capsulatus*: distribution and properties of Methane-Dependent Reduced Nicotinamide Adenine Dinucleotide Oxidase (methane hydroxylase)") and Ribbons and Michalover, FEBS Lett. 11:41–44 (1970) "Methane Oxidation by Cell-Free Extracts of *Methylococcus capsulatus*" or *Methylomonas capsulatus* by Ferenci (FEBS Lett. 41:94–98 (1974) "Carbon Monoxide-Stimulated Respiration in Methane-Utilizing Bacteria") suggested that the enzyme responsible for this oxygenation is a monooxygenase. These workers relied on indirect enzyme assays, measuring methane-stimulated NADH disappearance spectrophotometrically or methane-stimulated $O_2$ disappearance polarographically. Recently, methane mono-oxygenase systems were partially purified from *Methylosinus trichosporium* OB3b (Tonge, Harrison and Higgins, *J. Biochem.* 161: 333–334 (1977) "Purification and Properties of the Methane Mono-Oxygenase Enzyme System From *Methylosinus trichosporium* OB3b"; and Tonge, Harrison, Knowles and Higgins, FEBS Lett., 58: 293–299 (1975) "Properties and Partial Purification of the Methane-Oxidizing Enzyme System From *Methylosinus trichosporium*") and *Methylococcus capsulatus* (Bath) (Colby and Dalton, *J. Biochem.*, 171: 461–468 (1978) "Resolution of the Methane Mono-Oxygenase of *Methylococcus capsulatus* (Bath) Into three Components" and Colby, Stirling and Dalton, *J. Biochem.*, 165: 395–402 (1977) "The Soluble Methane Mono-Oxygenase of *Methylococcus capsulatus* (Bath), Its Ability to Oxygenate n-Alkanes, n-Alkenes, Ethers, and Alicyclic, Aromatic and Hetero-Cyclic Compounds").

BRIEF DESCRIPTION OF THE PRESENT INVENTION

It has now been discovered that lower $\alpha$-olefins, lower branched olefins, vinyl aromatic compounds and lower dienes, especially propylene, can be prepared by a low energy intensive process comprising contacting said olefins, vinyl aromatic compounds or dienes under aerobic conditions in the presence of microorganisms or enzyme preparations derived therefrom, wherein said microorganisms have been cultivated in a mineral nutrient medium containing methane. The microorganisms used in the process are preferably derived from the genera: Methylosinus, Methylocystis, Methylomonas, Methylobacter, Methylococcus and Methylobacterium.

Unlike the silver-catalyzed "direct oxidation" process for preparing ethylene oxide, it has been further discovered that the methane-grown methylotrophic microorganisms or an enzyme preparation derived therefrom are capable of epoxidizing $\alpha$-olefins having two to four carbon atoms and dienes, but are not capable of epoxidizing $C_{5+}$ $\alpha$-olefins (at least in amounts which are easily detectable by ordinary analytical methods). As a preferred embodiment the methane-induced methylotrophic microorganisms or the enzyme preparations derived therefrom are used to oxidatively convert propylene to propylene oxide.

DETAILED DESCRIPTION OF THE INVENTION

The term "microorganism" is used herein in its broadest sense to include not only bacteria, but also yeasts, filamentous fungi, actinomycetes and protozoa, and genetically engineered derivatives of these organisms. Preferably, the microorganisms will include bacteria capable of oxidizing methane and genetically engineered derivatives of bacteria.

The term "enzyme preparation" is used to refer to any composition of matter that exhibits the desired oxygenase enzymatic activity. The term is used to refer, for example, to live whole cells, dried cells, cell extracts, and refined and concentrated preparations derived from the cells. Enzyme preparations may be either in dry or liquid form. The term also includes the immobilized form of the enzyme, e.g., the whole cells of the methane grown microorganism or enzyme extracts immobilized or bound to an insoluble matrix by covalent chemical linkages, sorption and entrapment of the enzyme within a gel lattice having pores large enough to allow the molecules of the substrate and of the product to pass freely, but small enough to retain the enzyme. The term "enzyme preparation" also includes enzymes retained within hollow fiber membranes, e.g., as disclosed and claimed in U.S. application Ser. No. 238,649, filed Mar. 27, 1972.

The term "particulate fraction" refers to the oxygenase enzyme activity in the precipitated or sedimented pellet of whole cells after centrifugation at 20,000 x g. for 1 hour or the precipitated or sedimented fraction of cell-free extracts of the methane grown microorganisms after centrifugation between 10,000 x g. and 80,000 x g. for 1 hour.

The instant invention includes the following features:

The isolates of methane-utilizing microbes of the invention include obligate (Type I and Type II) and facultative bacteria as well as new methane-utilizing yeasts.

In addition to their ability to oxidize methane to methanol, resting cell-suspensions of several distinct types of methane-grown bacteria (e.g., Type I, obligate; Type II, obligate; and facultative) oxidize α-olefins, vinyl aromatic compounds and dienes to their corresponding 1,2-epoxides.

The product 1,2-epoxides are not further metabolized and accumulate extracellularly.

Methanol-grown cells do not have either the epoxidation or the hydroxylation activities. Among the substrate gaseous alkenes, propylene is oxidized at the highest rate.

Methane inhibits the epoxidation of propylene.

The stoichiometry of the consumption of propylene and oxygen, and the production of propylene oxide is 1:1:1.

Results from inhibition studies indicate that the same mono-oxygenase system catalyzes both the hydroxylation and the epoxidation reactions.

Both the hydroxylation and epoxidation activities are located in the cell-free (enzyme extract) particulate fraction precipitated or sedimented between 10,000 x g. and 80,000 x g. centrifugation for 1 hour.

Cell-free particulate fractions from the obligate and facultative methylotroph microorganisms catalyze the hydroxylation of methane to methanol and the epoxidation of lower α-olefins, branched lower olefins and alkanes, and dienes (e.g. ethylene, propylene, 1-butene, isobutylene, 2-methyl-1-butene, 3-methyl-1-butene, vinyl aromatic compounds, 2,2-dimethylpropane, isoprene and butadiene) in the presence of oxygen and reduced nicotinamide adenine dinucleotide (NADH) and the hydroxylation of $C_1$-$C_4$ n-alkanes (e.g., methane, ethane, propane and butane).

The hydroxylation and epoxidation activities of the methane-grown methylotrophs are lost simultaneously during storage and are strongly inhibited by various metal-binding agents.

The stoichiometry for the consumption of substrate (propylene or methane), oxygen, NADH, and product formation was found to be approximately 1:1:1:1.

The classification system of methane-oxidizing bacteria proposed by R. Whittenbury, K. C. Phillips and J. F. Wilkinson[J. Gen. Microbiology, 61, 205–218 (1970) (hereinafter Whittenbury et al)] is the most widely recognized system used today. In this system of classification, the morphological characteristics of methane-utilizing bacteria are divided into five groups. They are: Methylosinus, Methylocystis, Methylomonas, Methylobacter and Methylococcus. Bacteria of these five groups reported by Whittenbury et al. utilize methane, dimethylether, and methanol for growth energy and they were all reported as strictly aerobic and gram-negative. They are also characterized as being non-endosporing, i.e., the ability to form cysts and exospores with complex fine structure and complex internal structure.

As one embodiment of the present invention, it has been discovered that microorganisms described by Whittenbury et al, when cultivated in the presence of methane, are capable of epoxidizing lower α-olefins, particularly propylene, in the presence of oxygen. These methane-utilizing microorganisms are generally known as "methylotrophs". The enzyme system or the preparations derived from these microorganisms are referred to herein as an "epoxidizing enzyme system" which is believed to be a "methane mono-oxygenase" and/or "methane hydroxylase". Thus, it is to be understood that the enzyme system or enzyme preparations thereof referred to herein as the "alkene epoxidase" or "propylene epoxidase" used to convert the α-olefins to 1,2-epoxides are the "epoxidizing enzyme system" believed to be methane mono-oxygenase or methane hydroxylase enzymes.

The methylotrophic microorganisms reported by Whittenbury et al. (the disclosure of which is incorporated herein by reference) are contemplated for use in the practice of the present invention. Specifically, one may use those methylotrophic microorganisms mentioned in Table 4, page 214 of the Whittenbury et al paper, i.e., those microorganisms identified as: *Methylosinus trichosporium, Methylosinus sporium, Methylocystis parvus, Methylomonas methanica, Methylomonas albus, Methylomonas streptobacterium, Methylomonas agile, Methylomonas rubrum, Methylomonas rosaceus, Methylobacter chroococcum, Methylobacter bovis, Methylobacter capsulatus, Methylobacter vinelandii, Methylococcus capsulatus* (including *Methylococcus capsulatus* Strain Bath referred to by J. Colby and H. Dalton, *J. Biochem.*, 157, 495–497 (1976)) and *Methylococcus capsulatus* Strain Texas referred to by D. W. Ribbons, *J. Bacteriol.*, 122, 1351–1363 (1975)), and *Methylococcus minimus*. These methylotrophic microorganisms may be used in the form of their whole cells, enzyme extracts thereof or immobilized preparations of those whole cells or enzyme tracts, such as by use of DEAE cellulose or ion exchange resin or porous alumina carriers.

Subcultures of some methylotrophic microorganisms described by Whittenbury et al have been deposited with the official depository of the U.S. Dept. of Agriculture, Agriculture Research Service, Nothern Regional Research Laboratory, Peoria, Ill. 61604, by depositing therein subcultures of each, and have received from the depository the individual NRRL strain designations as indicated below. These subcultures have been deposited in accordance with the procedures of the Dept. of Agriculture without any restriction such that progeny of these strains are available to the public, including but not limited to those citizens in the United States of America and those citizens in West Germany. Strains of methylotrophic microorganisms deposited are identified as follows:

| Culture | USDA Agricultural Research Service Designation |
| --- | --- |
| *Methylosinus trichosphorium* OB3b | NRRL B-11,196 |
| *Methylosinus sporium* 5 | NRRL B-11,197 |
| *Methylocystis parvus* OBBP | NRRL B-11,198 |
| *Methylomonas methanica* $S_1$ | NRRL B-11,199 |
| *Methylomonas albus* BG8 | NRRL B-11,200 |
| *Methylobacter capsulatus* Y | NRRL B-11,201 |

Progeny of these strains are available to anyone who requests the same without any restriction as to availability. Subcultures of the aforementioned strains were originally obtained from R. Whittenbury, Department of Biological Science, University of Warwick, Warwickshire, Coventry, England.

The morphological and taxonomical characteristics of the above-mentioned methylotrophic strains are as follows:

*Methylosinus trichosporium* OB3b NRRL B-11,196

Produces white colonies on salt agar plates in the presence of methane or methanol. The organisms are motile, rod-shaped, gram-negative and aerobic. Rosettes are frequently formed. Has a Type II membrane structure.

*Methylosinus sporium* 5 NRRL B-11,197

Produces white colonies on salt agar plates in the presence of methane or methanol. The organisms are motile, rod-shaped, gram-negative and aerobic. Rosettes are frequently formed. Organisms form exospores which are heat-resistant; spores budded off the non-flagellated poles of the organisms which assumed a vibrio shape. Organic compounds other than methane and methanol do not support growth. Has a Type II membrane structure.

*Methylocystis parvus* OBBP NRRL B-11,198

Produces mucoid white colonies on salt agar plates in the presence of methane or methanol. The organisms are non-motile, cocco-bacillus in shape, gram-negative and aerobic. Organisms form cysts which are dessication-resistant, but not heat resistant. Grows at the expense of methane or methanol. Organic compounds other than methane and methanol do not support growth. Has a Type II membrane structure.

*Methylomonas methanica* $S_1$ NRRL B-11,199

Produces pink colonies on salt-agar plates in the presence of methane or methanol. The organisms are motile, rod-shaped, gram-negative and aerobic. Produces slimy capsules. They grow at the expense of methane and methanol. Organic compounds other than methane and methanol do not support growth. Has a Type I membrane structure.

*Methylomonas albus* BG8 NRRL B-11,200

Produces white colonies on salt-agar plates in the presence of methane or methanol. The organisms are motile, rod-shaped, gram-negative and aerobic. Produces slimy capsule. Grows at the expense of methane and methanol. Organic compounds other than methane and methanol do not support growth. Has a Type I membrane structure.

*Methylobacter capsulatus* Y NRRL B-11,201

Produces white to brown colonies on salt-agar plates in the presence of methane or methanol. The organisms are motile, rod-shaped, gram-negative and aerobic. Produces slimy capsule. Grows at the expense of methane and methanol. Organic compounds other than methane and methanol do not support growth. Has a Type I membrane structure.

Recently, Patt, Cole and Hanson (*International J. Systematic Bacteriology*, 27 (2) 226–229 (1976)) disclosed that methylotrophic bacteria are those bacteria that can grow non-autotrophically using carbon compounds containing one or more carbon atoms, but containing no carbon-carbon bonds. Patt et al have proposed that methylotrophs should be considered "obligate" if they are capable of utilizing only carbon compounds containing no carbon-carbon bonds (e.g., methane, methanol, dimethylether, methylamines, etc.) as the sole sources of carbon and energy whereas "facultative" methylotrophs are those organisms that can use compounds containing no carbon-carbon bonds and complex compounds containing carbon-carbon bonds as the sole sources of carbon and energy. In their paper, Patt et al. disclosed a methane-oxidizing bacterium, which they identified as *Methylobacterium organophilum* sp nov. (ATCC 27,886). This bacterium presumably differs from all previously described genera and species of methane-oxidizing bacteria because of its ability to utilize a variety of organic substrates with carbon-carbon bonds as sources of carbon and energy.

As another embodiment of the present invention, it has been discovered that this microorganism (*Methylobacterium organophilum* sp nov. ATCC 27,886) and other facultative methylotrophic microorganisms are also capable of epoxidizing $C_2$–$C_4$ alkenes. In other words, they possess alkene epoxidase enzyme activity when cultivated in the presence of methane. As discussed above with respect to the Whittenbury et al methylotrophic microorganisms, the facultative methylotrophs may be used in the form of their crude extract (i.e. supernatent after centrifuging broken cells at 10,000×g. for 30 min.) or may be placed in immobilized form or used in the cell-bound form when put to use in the process of the present invention.

Other known methylotrophic strains may be used in the process of the present invention, e.g., Methylomonas sp. AJ-3670 (FERM P-2400) referred to in U.S. Pat. No. 3,930,947 as freely available from the Fermentation Research Institute, Agency of Industrial Science and Technology, Ministry for Industrial Trade and Industry, Chiba, Japan; and Methylococcus 999 referred to in U.S. Pat. No. 4,042,458 as having NCIB Accession No. 11083 as well as Methylomonas SM3 having NCIB Accession No. 11084 (which has been described in Netherlands patent application No. 74/16644). Mixtures of methylotrophic and non-methylotrophic microorganisms may be utilized, such as the systems described in U.S. Pat. Nos. 3,996,105 and 4,042,458.

In commercial processes for the propagation of microorganisms, it is generally necessary to proceed by stages. These stages may be few or many, depending on the nature of the process and the characteristics of the microorganisms. Ordinarily, propagation is started by inoculating cells from a slant of a culture into a presterilized nutrient medium usually contained in a flask. In the flask, growth of the microorganisms is encouraged by various means, e.g., shaking for thorough aeration, and maintenance of suitable temperature. This step or stage is repeated one or more times in flasks or vessels containing the same or larger volumes of nutrient medium. These stages may be conveniently referred to as culture development stages. The microorganisms with or without accompanying culture medium, from the last development stage, are introduced or inoculated into a large scale fermentor to produce commercial quantities of the microorganisms or enzymes therefrom.

Reasons for growing the microorganisms in stages are manyfold, but are primarily dependent upon the conditions necessary for the growth of the microorganisms and/or the production of enzymes therefrom. These include stability of the microorganisms, proper nutrients, pH, osmotic relationships, degree of aeration, temperature and the maintenance of pure culture conditions during fermentation. For instance, to obtain maximum yields of the alkene epoxidase, the conditions of fermentation in the final stage may have to be changed somewhat from those practiced to obtain growth of the microorganisms in the culture development stages. Maintaining the purity of the medium, also, is an extremely important consideration, especially where the fermentation is performed under aerobic conditions as in the case of the methylotrophic microorganisms. If the fermentation is initially started in a large fermentor, a relatively long period of time will be needed to achieve an appreciable yield of microorganisms and/or alkene epoxidase enzyme therefrom. This, of course, enhances the possibility of contamination of the medium and mutation of the microorganisms.

The culture media used for growing the methylotrophic microorganisms and inducing the oxygenase or epoxidation enzyme system will be comprised of inorganic salts of phosphate, sulfates and nitrates as well as oxygen and a source of methane. The fermentation will generally be conducted at temperatures ranging from 5° to about 55° C., preferably at temperatures ranging from about 25° to about 50° C. The pH of the culture medium should be controlled at a pH ranging from about 4 to 9 and preferably from about 5.5 to 8.5 and more preferably from 6.0 to 7.5. The fermentation may be conducted at atmospheric pressure although higher pressures up to about 5 atmospheres and higher may be employed.

Typically, to grow the methylotrophic microorganisms and to induce the oxygenase or epoxidation enzyme system the microorganisms are inoculated into the medium which is contacted with a gas mixture containing methane and oxygen. Methane may be supplied in the form of natural gas. For continuous flow culture the microorganisms may be grown in any suitably adapted fermentation vessel, for example, a stirred baffled fermentor or sparged tower fermentor, which is provided either with internal cooling or an external recycle cooling loop. Fresh medium may be continuously pumped into the culture at rates equivalent to 0.02 to 1 culture volume per hour and the culture may be removed at a rate such that the volume of culture remains constant. A gas mixture containing methane and oxygen and possibly carbon dioxide or other gases is contacted with the medium preferably by bubbling continuously through a sparger at the base of the vessel. The source of oxygen for the culture may be air, oxygen or oxygen-enriched air. Spent gas may be removed from the head of the vessel. The spent gas may be recycled either through an external loop or internally by means of a gas inducer impeller. The gas flows and recycle should be arranged to give maximum growth of microorganism and maximum utilization of methane.

The oxygenase enzyme system may be obtained, as described above, as a crude extract, or a cell-free particulate fraction, i.e., the material which precipitates or sediments when the supernatant after centrifuging broken cells at 10,000×g. for 30 min. is centrifuged for 1 hour at 10,000 ×g. or greater. The microbial cells may be harvested from the growth medium by any of the standard techniques commonly used, for example, flocculation, sedimentation, and/or precipitation, followed by centrifugation and/or filtration. The biomass may also be dried, e.g., by freeze or spray drying and may be used in this form for further use in the epoxidation reaction. When using the cell-free enzyme, NADH and a metal (e.g., copper or iron), may be added to enhance the enzyme activity. Methane or a methane metabolite may be added as electron donor to further enhance the conversion when using cells or a cell-free system.

To put the invention to practice, an oxygenase enzyme system is obtained, such as, for example, in the manner described above, which will convert methane to methanol under oxidative conditions. The source of the enzyme is not critical, but it is preferred to obtain such a preparation from one of the five genera of microorganisms disclosed in the Whittenbury et al. paper or from the facultative methylotrophs (Methylobacterium) and grow the microorganism in a nutrient medium containing methane and oxygen as described above. The nutrient medium may be the one described by Whittenbury et al. or more preferably the culture medium described by Foster and Davis, *J. Bacteriol*, 91, 1924–1931 (1966). The enzyme preparation is then brought into contact with an α-olefin or diene, e.g., ethylene, propylene, butene-1, isobutylene, 2-methyl-1-butene, 3-methyl-1-butene, vinyl aromatic compounds such as styrene, or conjugated butadiene, isoprene, 2,2-dimethylpropane or mixtures thereof in the presence of oxygen in a buffer solution and the mixture is incubated until the desired degree of conversion has been obtained. Thereafter, the epoxide is recovered by conventional means, e.g., distillation, etc.

To facilitate the necessary effective contact of oxygen and the enzyme (whether it be an enzyme preparation or methylotrophic microorganisms), it is preferred, for best results, to employ a strong, finely divided air stream into a vigorously stirred dispersion of olefin in the epoxidation medium that generally contains water and a buffer, and in which the enzyme preparation or microorganism culture is suspended. The enzyme preparation may then be separated from the liquid medium, preferably by filtration or centrifugation. The resulting epoxide may then generally be obtained. Preferably, the epoxidation is carried out at a temperature in the range from about 5° to about 55° C., more preferably, from about 25° to about 50° C., and at a pH in the range from about 4 to about 9, more preferably from 5.5 to 7.5.

The process of the invention may be carried out batch-wise, semi-continuously, continuously, concurrently or countercurrently. Optionally, the suspension containing the enzyme preparation or methylotrophic microorganisms and a buffer solution is passed downwardly with vigorous stirring countercurrently to an air stream rising in a tube reactor. The top layer is removed from the downflowing suspension, while culture and remaining buffer solution constituents are recycled, at least partly, with more olefin and addition of fresh enzyme preparation or methylotrophic microorganism, as required.

The growth of the methylotrophic microorganisms and the epoxidation process may be conveniently coupled by conducting them simultaneously, but separately and using much higher aeration in the epoxidation process (e.g., an air excess of at least twice that required for growth, preferably at least five times as much aeration). Both the growth process and epoxidation process may be conducted in the same reactor in sequential or simultaneous operations by alternate use of normal and strong aeration.

The invention is illustrated further by the following examples which, however, are not to be taken as limiting in any respect. All parts and percentages, unless expressly stated otherwise, are by weight.

EXAMPLE 1

A nutrient medium as described by Foster and Davis, *J. Bacteriol.*, 91, 1924–1931 (1966) having the following composition per liter was prepared.

| | |
|---|---|
| $Na_2HPO_4$ | 0.21 g |
| $NaH_2PO_4$ | 0.09 g |
| $NaNO_3$ | 2.0 g |
| $MgSO_4.7H_2O$ | 0.2 g |
| $KCl$ | 0.04 g |
| $CaCl_2$ | 0.015 g |
| $FeSO_4.7H_2O$ | 1.0 mg |
| $CuSO_4.5H_2O$ | 0.01 mg |
| $H_3BO_4$ | 0.02 mg |
| $MnSO_4.5H_2O$ | 0.02 mg |
| $ZnSO_4$ | 0.14 mg |
| $MoO_3$ | 0.02 mg |

The pH of the nutrient medium was adjusted to 7.0 by the addition of acid or base and 50 ml aliquots of the nutrient medium was charged into a plurality of 300 ml shake flasks. The shake flasks were inoculated with an inoculating loop of cells from an agar plate containing homogeneous colonies of the microorganisms on the plate (the purity of the isolates were confirmed by microscopic examination). The isolates had been maintained on agar plates under an atmosphere of methane and air having a 1:1 v/v gas ratio which had been transferred every two weeks. The gaseous phase of the inoculated flasks was then replaced with a gas mixture comprised of methane and air having a ratio of 1:1 on a v/v basis. The inoculated flasks were sealed air tight and were incubated on a rotary shaker of orbital radius 2.5 cm at 250 rpm and at 30° C. for two days until the turbidity in the medium had developed.

The cells were harvested by centrifugation at 10,000 ×g at 4° C. for 30 minutes. The cell pellet was washed twice with a 0.15 M phosphate buffer at a pH of 7.0 (containing 0.002 M $MgCl_2$). The washed cells were then suspended in a 0.15 M phosphate buffer at pH 7.0.

A 0.5 ml aliquot of each washed cell suspension (2 mg cells) was put into 10 ml vials at 4° C. which were sealed with a rubber cap. The gaseous phase of the vials was removed with vacuum and then was replaced with a gas mixture of alkene and oxygen at a 1:1 v/v ratio. It was then incubated at 30° C. on a rotary shaker at 300 rpm. Samples of product (3 μl) were withdrawn periodically with a microsyringe and the products were analyzed by gas chromatography (ionization flame detector column).

Table I shows the conversion rates for the hydroxylation of methane and the epoxidation of propylene by washed cell suspensions of several microorganisms, strains which had been grown on methane by the experimental procedure described above. It can be seen from these data that the methane-grown microorganisms which are capable of hydroxylating methane to methanol are also capable of converting propylene to propylene oxide.

TABLE I
CONVERSION RATES FOR METHANE HYDROXYLATION AND PROPYLENE EPOXIDATION

| | Conversion Rates (μmole/hr/mg protein)[a] | |
|---|---|---|
| Microorganism Strains[b] | Methane Hydroxylation | Propylene to Propylene Oxide |
| *Methylosinus trichosporium* OB3b (NRRL B-11,196) | 1.5 | 3.6 |
| *Methylosinus sporium* 5 (NRRL B-11,197) | 1.1 | 2.0 |
| *Methylocystis parvus* OBBP (NRRL B-11,198) | 0.7 | 1.6 |
| *Methylomonas methanica* $S_1$ (NRRL B-11,199) | 1.3 | 2.7 |
| *Methylomonas albus* BG8 (NRRL B-11,200) | 1.8 | 1.4 |
| *Methylobacter capsulatus* Y (NRRL B-11,201) | 1.2 | 1.5 |
| *Methylobacterium organophilum* XX (ATCC 27,886) | 1.0 | 1.8 |

[a] The methanol and propylene oxide products were identified by gas chromatographic retention time comparisions with authenic standards.
[b] The dry weight of the cells was about 0.2 g/100 ml of culture broth.

Table II shows the conversion rates for the hydroxylation of methane and the epoxidation of propylene (from Table I) and the epoxidation of ethylene, butene-1 and butadiene by washed cell suspensions of two microorganism strains which had been grown on methane by the experimental procedure described above. These methane-grown microorganisms, when contacted with pentene-1 and hexene-1 in the presence of air, did not produce any detectable epoxide. Also, it can be seen from the data that the conversion rates for propylene to propylene oxide were higher for the respective methane-grown microorganism than for the other conversions.

TABLE II
CONVERSION RATES FOR METHANE HYDROXYLATION AND EPOXIDATION OF α-OLEFINS

| | Conversion Rates (μmole/hr/mg protein)[a] | | | | | | |
|---|---|---|---|---|---|---|---|
| Microorganism Strains[b] | Methane to Methanol | Ethylene to Ethylene Oxide | Propylene to Propylene Oxide | Butene-1 to 1,2-epoxy-butane | Butadiene to 1,2-epoxy-butene | Pentane-1 to 1,2-epoxy-pentane | Hexene-1 to 1,2-epoxy-hexane |
| *Methylosinus trichosporium* OB3b (NRRL B-11,196) | 1.5 | 1.9 | 3.6 | 0.45 | 2.6 | 0 | 0 |
| *Methylosinus sporium* 5 (NRRL B-11,197) | 1.8 | 1.1 | 2.0 | 0.8 | 1.5 | 0 | 0 |

[a] The products were identified by gas chromatographic retention time comparisons with authenic standards. (The identification of the products was supplemented by establishing the presence or absence of product peaks before and after bromination or acid hydrolysis. Analysis also revealed that no further oxidation of the epoxide product occurred).
[b] The dry weight of the cells was about 0.2 g/100 ml culture broth.

The experimental procedure described above was repeated in the case of the strains *Methylocystis parvus* OBBP (NRRL B-11,198), *Methylomonas methanica* $S_1$ (NRRL B-11,199) and *Methylomonas albus* BG8 (NRRL B-11,200) and washed cell suspensions of these methane-grown microorganisms were successfully used to convert ethylene to ethylene oxide at conversion rates of 0.9, 0.95 and 1.2 μmole/hr/mg protein at a 0.2 g/100 ml dry weight of cells per culture broth basis, respectively.

As shown above, a novel method has been discovered whereby propylene oxide is obtained by incubating propylene in the presence of cells or cell-free extracts of microorganisms (or enzymes derived therefrom) which have been grown in the presence of methane. These microorganisms are known to be able to hydroxylate short chain alkanes (e.g., methane to methanol) and some investigators have suggested they may be capable of epoxidizing ethylene. It has now been discovered that these methane-grown microorganisms and their enzyme preparations have the ability to epoxidize propylene at relatively higher conversion rates than in the case of ethylene, butene-1 and butadiene. In batch experiments using washed, methane-grown cells, the epoxidation reaction proceeds linearly for at least 2 hours. No further oxidation of the epoxide product was detected.

The epoxidation enzyme system of the methane-grown microorganisms is inducible (by the methane) and the epoxide product accumulates extracellularly (i.e., after the reaction, the reaction mixture was centrifuged and the epoxide product was only found in the supernatant fraction and not in the cell pellet). The possibility of propanal as an oxidation product of propylene was ruled out as a result of g.l.c. analysis.

In comparative experimental tests, washed cell suspensions of the methanol-grown microorganism strains *Methylosinus trichosporium* OB3b (NRRL B-11,196), *Methylocystis parvus* OBBP (NRRL B-11,198), *Methylomonas methanica* $S_1$ (NRRL B-11,199) and *Methylobacter capsulatus* Y (NRRL B-11,201) did not possess the ability for either the hydroxylation of methane or the ability to epoxidize $C_2$-$C_4$ alkenes, particularly propylene. From the evidence shown, only the methane-grown microorganisms possess both methane hydroxylation and $C_2$-$C_4$ epoxidation abilities.

As previously indicated both the whole cells and the cell-free extracts containing the oxygenase enzyme activity of the methane grown methylotrophs may be used in the hydroxylation and epoxidation reactions in the presence of air. NADH and metal (iron or copper) may be added to enhance activity when the cell-free or pure enzyme preparations are used. In utilizing the cell-free enzyme system of the invention the enzyme preparations were prepared as follows.

Preparation of Cellular Fractions

Organisms were grown at 30° C. in 2.8 liter flasks containing 700 ml mineral salts medium as described in Example 1 with methane (methane and air, 1:1 parts by volume) as the sole carbon and energy source. Cells were harvested during exponential growth by centrifugation at 12,000×g. for 15 min. at 4° C. Cells were washed twice with 25 mM potassium phosphate buffer, pH 7.0 containing 5 mM $MgCl_2$. Cells were suspended in the same buffer. The cell suspensions at 4° C. were disintegrated by a single passage through a French Pressure cell (15,000 lb./in.$^2$) and centrifuged at 5000×g. for 15 min. to remove unbroken bacteria. The supernatant solution (crude extract) was then centrifuged at 40,000×g. for 30 min., yielding particulate P(40) and soluble S(40) fractions. The S(40) fraction was subsequently centrifuged at 80,000×g. for 60 min., yielding particulate P(80) and soluble S(80) fractions. The particulate fractions [P(40) and P(80)] were suspended in 25 mM potassium phosphate buffer, pH 7.0, containing 5 mM $MgCl_2$ and homogenized at 4° C.

Enzyme Assay

The oxidation of methane and propylene by particulate [(P)40 and (P)80] fractions and soluble [S(80)] fraction was measured at 30° C. by estimating the production of methanol and propylene oxide, respectively. The reaction mixtures contained in 1.0 ml: 150 mM potassium phosphate buffer, pH 7.0 containing 5 mM $MgCl_2$, 0.6 ml; 10 moles NADH, and cellular fraction.

Reaction mixtures were contained in 10 ml vials at 4° C. Vials were sealed with rubber caps. The gaseous phase in the vials was removed using vacuum and then was replaced with a gas mixture of methane or propylene and oxygen at a 1:1, v/v ratio. Oxidation of other gaseous n-alkanes and n-alkenes was examined as described above. For liquid substrates, 10 μl of substrate was used directly. Vials were then incubated at 30° C. on a rotary shaker at 200 RPM.

The products of epoxidation of n-alkenes and hydroxylation of n-alkanes were assayed by flame ionization gas chromatography using a stainless steel column (12'×⅛") packed with 10% Carbowax 20 M on 80/100 Chromosorb W and Porapak Q column. The column temperature was maintained isothermally at 120° C. The carrier gas flow rate was 30 ml/min. of helium. The various products were identified by retention time comparisons and co-chromatography with authentic standards.

Specific activities were expressed as μ moles of products formed per hour per mg. protein. Concentrations of protein in various fractions were determined by the method of Lowry et al., *J. Biol. Chem.* 193: 265–275 (1951).

Distribution of n-Alkanes- and n-Alkenes-Oxidizing Activities in Cell-Fractions

Three distinct groups of methane-utilizing organisms were selected to examine oxidation of n-alkanes ($C_1$-$C_4$) and n-alkenes ($C_2$-$C_4$) in cell-free systems. Cellular fractions were prepared from Type I obligate methane-utilizing organisms, Methylomonas sp. (CLR-17, NRRL B-11,208) and *Methylococcus capsulatus* (Texas, ATCC 19,069); Type II obligate methane-utilizing organisms, *Methylosinus trichosporium* (OB3b, NRRL B-11,196) and Methylosinus sp. (CRL-15, NRRL B-11,202); and a facultative methane-utilizing bacterium, Methylbacterium sp. (CRL-26, NRRL B-11,222).

Table III shows the distribution of the methane- and propylene-oxidixzing activity in various fractions derived from these organisms. About 85–90% of the total activity was detected in the P(40) fraction and 10% was detected in the P(80) fraction. The soluble fraction S(80) did not contain any activity. The specific activities for the methane and the propylene oxidation in fractions P(40) and P(80) did not vary significantly in the various organisms examined (Table IV). Epoxidation of propylene and hydroxylation of methane were both dependent upon the presence of oxygen and NADH. NADPH or ascorbate and other electron carriers could also be utilized. Both reactions were linear during the first 15 min. as measured by detection of product by gas chromatography.

TABLE III

DISTRIBUTION OF PROPYLENE - AND METHANE-OXIDIZING ACTIVITIES IN CELL FRACTIONS OF METHYLOTROPHS

| | % Distribution in Cell Fraction | | | | | |
|---|---|---|---|---|---|---|
| | Propylene-Epoxidizing[a] Activity | | | Methane-Hydroxylating[a] Activity | | |
| Microorganism | P(40) | P(80) | S(80) | P(40) | P(80) | S(80) |
| Type I Obligate Methylotrophs | | | | | | |
| Methylomonas sp. (CRL-17, NRRL B-11,208) | 85 | 15 | 0 | 87 | 13 | 0 |
| Methylococcus capsulatus (Texas, ATCC 19,069) | 89 | 11 | 0 | 90 | 10 | 0 |
| Type II Obligate Methylotrophs | | | | | | |
| Methylosinus sp. (CRL-15, NRRL B-11,202) | 87 | 13 | 0 | 88 | 12 | 0 |
| Methylosinus trichosporium (OB3b, NRRL B-11,196) | 82 | 18 | 0 | 83 | 13 | 0 |
| Facultative Methylotroph | | | | | | |
| Methylobacterium sp. (CRL-26, NRRL B-11,222) | 85 | 15 | 0 | 82 | 18 | 0 |

[a]Reactions were carried out as described in Example 1. The product of reaction was estimated by gas chromatography after 5, 10 and 15 min. of incubation of reaction mixture at 30° C. on a rotary shaker.

TABLE IV

THE RATE OF METHANE HYDROXYLATION - AND PROPYLENE-EPOXIDATION IN THE CELL-FRACTIONS OF METHYLOTROPHS

| | Cell Fraction | | | | | |
|---|---|---|---|---|---|---|
| | Propylene-Oxidizing[a] Activity | | | Methane-Oxidizing[a] Activity | | |
| Microorganism | P(40) | P(80) | S(80) | P(40) | P(80) | S(80) |
| Type I Obligate Methylotroph | | | | | | |
| Methylomonas sp. (CRL-17, NRRL B-11,208) | 2.2 | 2.0 | 0 | 2.9 | 2.7 | 0 |
| Methylococcus capsulatus (Texas, ATCC 19,069) | 2.6 | 2.0 | 0 | 3.8 | 3.9 | 0 |
| Type II Obligate Methylotroph | | | | | | |
| Methylosinus sp. (CRL-15, NRRL B-11,202) | 3.8 | 3.7 | 0 | 4.8 | 4.2 | 0 |
| Methylosinus trichosporium (OB3b, NRRL B-11,196) | 2.8 | 2.5 | 0 | 3.1 | 3.0 | 0 |
| Facultative methylotroph | | | | | | |
| Methylobacterium sp. (CRL-26, NRRL B-11,222) | 1.2 | 1.1 | 0 | 2.7 | 2.8 | 0 |

[a]Reactions were carried out as described in Example 1. The product of the reaction was estimated by gas chromatography after 5, 10 and 15 min. of incubation of reaction mixtures at 30° C. on a rotary shaker. The rate of oxidation is expressed as μmoles of product formed per hr. per mg. of protein.

The particulate fractions [P(40) and P(80)] from various organisms also catalyzed the epoxidation of other n-alkenes (ethylene, 1-butene, and 1,3-butadiene) to the corresponding 1,2-epoxides and the hydroxylation of methane and ethane to the corresponding alcohols. Table V shows the rate of oxidation of various n-alkanes and n-alkenes by the P(40) particulate fraction of Methylosinus sp. (CRL-15, NRRL B-11,202). The product of oxidation was identified by gas chromatography after incubating P(40) fraction with various substrates at 30° C. for b 10 min.

TABLE V

OXIDATION OF n-ALKENES AND n-ALKANES BY P(40) PARTICULATE FRACTION OF METHYLOSINUS SP. (CRL-15, NRRL B-11,202)

| Substrate | Product | Rate of Product Formation[a] (μmoles/hr/mg of protein) |
|---|---|---|
| Ethylene | Ethylene Oxide | 1.27 |
| Propylene | Propylene Oxide | 4.1 |
| 1-Butene | Epoxy butane | 2.18 |
| Butadiene | Epoxy butene | 0.63 |
| 1-Pentene | — | 0 |
| Methane | Methanol | 4.8 |
| Ethane | Ethanol | 3.2 |

[a]Reactions were carried out as described in Example 1. The product of the reaction was estimated by gas chromatography after 5, 10, and 15 min. of incubation of reaction mixture at 30° C. on a rotary shaker.

Methylosinus sp. (CRL-15, NRRL B-11,202) was selected for further studies on the influence of various environmental factors on the methane- and propylene-oxidizing activities in cell-free systems.

Effect of Particulate Fraction Concentration

The effect of the P(40) particulate fraction concentration on the hydroxylation of methane and epoxidation of propylene was examined. The production of methanol and propylene oxide was directly dependent upon the concentration of particulate fraction ranging from 1-6 mg. of protein per ml. The rate of reaction was decreased upon further increasing the particulate protein concentration to 8 mg./ml.

Time Course of Reactions

The rate of formation of methanol and propylene oxide by hydroxylation of methane and epoxidation of propylene respectively, by the P(40) particulate fraction of Methylosinus sp. (CRL-15, NRRL B-11,202) was linear with time up to 15 minutes.

Effect pH

The effect of pH on the hydroxylation of methane and epoxidation of propylene by the P(40) particulate fraction of Methylosinus sp. (CRL-15, NRRL B-11,202) was examined by estimating the amount of methanol and propylene oxide formed after 10 min. incubation of reaction mixtures. The optimum pH for both hydroxylation of methane and epoxidation of propylene was found to be 7.0. In carrying out these tests the reactions were carried out as described in Example 1. The product of reaction was estimated by gas chromatography after 5, 10 and 15 minutes of incubation of reaction mixture at 30° C. on a rotary shaker. 100% activity equals 4.8 and 4.1 $\mu$moles of methanol or propylene oxide formed respectively, per hour, per mg protein.

Effect of Temperature

The effect of temperature on the production of methanol and propylene oxide by the P(40) particulate fraction of Methylosinus sp. (CRL-15, NRRL B-11,202) was examined after incubation of reaction mixtures for 10 min. at various temperatures. The optimum temperature for epoxidation of propylene and hydroxylation of methane was found to be 35° C. In carrying out these tests the reactions were carried out as described in Example 1. The product of reaction was estimated by gas chromatography after 5, 10 and 15 minutes of incubation of reaction mixture at 30° C. on a rotary shaker. 100% activity equals 5.0 and 4.2 $\mu$moles of methanol and propylene oxide formed respectively, per hour per mg of protein.

Effect of Storage

It was noted that both the activity for hydroxylation of methane and the epoxidation of propylene by the P(40) particulate fraction of Methylosinus sp. (CRL-15, NRRL B-11,202) decreased simultaneously when stored at refrigerator (0°–4° C.) temperature. In carrying out these tests the reactions were carried out as described in Example 1. The product of reaction was estimated by gas chromatography after 5, 10 and 15 minutes incubation of the reaction mixture at 30° C. on a rotary shaker. 100% activity equals 4.8 and 4.1 $\mu$moles of methanol and propylene oxide formed respectively per hr. per mg. of protein.

Effect of Inhibitors

It has been reported that the oxidation of methane by cell suspensions of methane-utilizing bacteria was inhibited by various metal-binding or metal-chelating agents (Patel et al., *J. Bacteriol.* 126: 1017–1019 (1976)). Hence, the effect of inhibitors on methane- and propylene-oxidizing activities by the P(40) particulate fraction of Methylosinus sp. (CRL-15, NRRL B-11,202) was examined. The production of methanol and propylene oxide was inhibited by various metal-binding compounds with different ligand combinations, i.e., nitrogen-nitrogen ($\alpha,\alpha$-bipyridyl), oxygen-nitrogen (8-hydroxyquinoline) and sulfur-nitrogen (thiourea, thiosemicarbazide) as shown in Table VI. This suggests the involvement of metal ion(s) in the oxidation of both hydroxylation of methane, and epoxidation of propylene. Similarly, as shown in Table VIa these compounds also inhibit the hydroxylation of methane and epoxidation of propylene when using cell-containing enzyme preparations.

TABLE VIa

Effect of Inhibitors on the Epoxidation of Propylene and the Hydroxylation of Methane

| | % Inhibition | | | | | |
|---|---|---|---|---|---|---|
| | Methylosinus trichosporium OB3b (NRRL B-11,196) | | Methylococcus capsulatus (CRL M1, NRRL B-11,219) | | Methylobacterium organophilum (CRL 26, NRRL B-11,222) | |
| Inhibitor | Epoxidation | Hydroxylation | Epoxidation | Hydroxylation | Epoxidation | Hydroxylation |
| Thiourea | 100 | 100 | 100 | 100 | 100 | 100 |
| 1,10-phenanthroline | 90 | 92 | 95 | 95 | 90 | 90 |
| $\alpha,\alpha$-Bipyridyl | 100 | 90 | 100 | 100 | 100 | 100 |
| Imidazole | 95 | 90 | 95 | 95 | 100 | 100 |
| Potassium cyanide | 100 | 100 | 100 | 100 | 95 | 95 |

The reactions were conducted as described in Example 1. The products were estimated by gas chromatography after 1 hour of incubation at 30° C. Each inhibitor was added at a final concentration of 1 mM.

TABLE VI

EFFECT OF INHIBITOR ON THE ACTIVITY FOR EPOXIDATION OF PROPYLENE AND HYDROXYLATION OF METHANE BY METHYLOSINUS SP. (CRL-15, NRRL B-11,202)

| | | % Inhibition[a] | |
|---|---|---|---|
| Inhibitor | Concentration (M) | Propylene-Epoxidizing Activity | Methane-Hydroxylating Activity |
| Control | — | 0 | 0 |
| $\alpha,\alpha$-Bipyridyl | $10^{-3}$ | 98 | 99 |
| 1,10-Phenanthroline | $10^{-3}$ | 93 | 90 |
| Potassium cyanide | $10^{-3}$ | 98 | 100 |
| Thiosemicarbazide | $10^{-3}$ | 97 | 100 |
| Thiourea | $10^{-3}$ | 98 | 98 |
| 8-Hydroxyquinoline | $10^{-3}$ | 75 | 80 |

[a]Reactions were carried out as described in Example 1. The product of the reaction was estimated by gas chromatography after 5, 10, and 15 min. incubation of the reaction mixture of 30° C. on a rotary shaker. The uninhibited rates of methane and propylene oxidation were 4.5 and 4.1 $\mu$moles of methanol and propylene oxide formed, respectively, per hr. per mg. of protein in P(40) fraction of Methylosinus sp. (CRL-15, NRRL B-11,202).

Effect of Metals

Since the methane mono-oxygenase from methane-utilizing bacteria is a copper or iron-containing protein (Tonge et al., *J. Biochem.*, 161: 333–344 (1977)), we have examined the effect of copper and iron salts on the oxidation of methane and propylene by the P(40) particulate fraction of Methylosinus sp. (CRL-15, NRRL B-11,202). The rate of hydroxylation of methane to methanol and epoxidation of propylene to propylene oxide was increased 2 fold in the presence of added copper salts (Table VII).

TABLE VII
EFFECT OF METALS ON THE ACTIVITY FOR EPOXIDIZING PROPYLENE AND HYDROXYLATING METHANE BY METHYLOSINUS SP. (CRL-15, NRRL B-11,202)

| Metal | Concentration (M) | Propylene-Oxidizing[a] Activity ($\mu$moles/hr/mg protein) | Methane-Oxidizing[a] Activity ($\mu$moles/hr/mg protein) |
|---|---|---|---|
| Control | — | 4.5 | 4.0 |
| Ferric Chloride | $10^{-3}$ | 5.8 | 4.8 |
| Ferrous Sulfate | $10^{-3}$ | 5.9 | 4.8 |
| Cuprous Chloride | $10^{-3}$ | 9.2 | 7.2 |
| Cupric Sulfate | $10^{-3}$ | 9.0 | 7.1 |

[a]Reactions were carried out as described in Example 1. The product of the reaction was estimated by gas chromatography after 5, 10 and 15 min. of incubation of the reaction mixture at 30° C. on a rotary shaker. The rates of oxidation were expressed as $\mu$moles of product formed per hr. per mg. of protein in P(40) fraction of Methylosinus sp. (CRL-15, NRRL B-11,202).

Substrate Competition Experiments

The hydroxylation of methane and the epoxidation of propylene by particulate fractions of methane-utilizing bacteria required oxygen and NADH. The question of whether the same or a similar enzyme was involved in the oxidation of both substrates was examined by substrate competition experiments. The experiment consisted of determining the effect of methane on the oxidation of propylene to propylene oxide by the P(40) particulate fraction of Methylosinus sp. (CRL-15, NRRL B-11,202). As shown in Table VIII, there was a reduction in the amount of propylene oxide formed in the presence of methane. Hence, methane inhibited the conversion of propylene to propylene oxide, presumably by competing for the available enzymatic site.

TABLE VIII
EFFECT OF METHANE ON PROPYLENE EPOXIDIZING ACTIVITY BY P(40) PARTICULATE FRACTION OF METHYLOSINUS SP. (CRL-15, NRRL B-11,202)

| Substrate | Propylene Oxide Produced[a] $\mu$moles/hr/mg. protein |
|---|---|
| Propylene | 4.3 |
| Propylene + Methane (1:1, v/v) | 1.8 |
| Methane | 0 |

[a]Reactions were carried out as described in Example 1. The product of the reaction was estimated by gas chromatography after 5, 10, and 15 min. of incubation of the reaction mixture at 30° C. on a rotary shaker.

Similarly, methane effects the epoxidation of propylene from cell-suspensions of methane-grown Methylosinus trichosporium OB3b (NRRL B-11,196) as shown in Table VIIIa.

TABLE VIIIa
EFFECT OF METHANE ON THE EPOXIDATION OF PROPYLENE[a]

| Composition of Gaseous Phase | Propylene Oxide Formed ($\mu$moles) | % Inhibition |
|---|---|---|
| Propylene + Helium + $O_2$ (25:25:50 v/v) | 1.6 | 0 |
| Propylene + Methane + $O_2$ (25:25:50 v/v) | 0.8 | 50 |

[a]The reactions were conducted as described in Example 1 except that various gaseous compositions were used to maintain a constant propylene partial pressure. Cell-suspensions of methane-grown Methylosinus trichosporium OB3b (NRRL B-11,196) (3.6 mg.) were used. Propylene oxide was estimated by gas chromatography after 15 minutes of the incubation.

Stoichiometry of Propylene and Methane Oxidation

The particulate P(40) fraction of Methylosinus sp. (CRL-15, NRRL B-11,202) was used to determine the stoichiometry of hydroxylation and epoxidation reactions. The stoichiometry of methane- or propylene-dependent NADH oxidation, oxygen consumption and product formation was approximately 1:1:1 [Table IX]. This is consistent with methane or propylene oxygenation being catalyzed by a mono-oxygenase.

TABLE IX
STOICHIOMETRY OF PROPYLENE EPOXIDATION AND METHANE HYDROXYLATION BY P(40) PARTICULATE FRACTION OF METHYLOSINUS SP. (CRL-15, NRRL B-11,202)[a]

| Substrate ($\mu$moles) | Product Formed ($\mu$moles) | NADH Oxidized ($\mu$moles) | $O_2$ Consumed ($\mu$moles) |
|---|---|---|---|
| Propylene 5.0 | Propylene Oxide 4.5 | 5.0 | 4.8 |
| Methane 5.0 | Methanol 4.2 | 4.8 | 4.6 |

[a]Under identical condition of reaction, the estimation of NADH oxidized was carried out spectrophotometrically, the estimation of oxygen consumed was measured polarographically, and the estimation of product formed was carried out by gas chromatography.

As a comparison the stoichiometry of the epoxidation of propylene by a cell-suspension of Methylosinus trichosporium OB3b (NRRL B-11,196) was determined as follows. The reaction mixture (3.0 ml.) contained 0.05 M sodium phosphate buffer, pH 7.0 and 3.6 $\mu$moles of propylene. The reaction was initiated by the injection of 0.1 ml. of cell-suspension (3.1 mg protein). A correction was made for the endogenous consumption of oxygen. The amount of oxygen consumed during the reaction (3 min.) was determined polarographically with a Clark oxygen electrode. The propylene consumed and the propylene oxide formed was estimated by gas chromatography. The propylene consumed was 0.29 $\mu$moles, the oxygen consumed was 0.30 $\mu$moles and the propylene oxide formed was 0.28 $\mu$moles.

To further demonstrate that the enzyme activity is in the particulate fraction (not in the supernatent) the following experiments were carried out. Cells of methane-grown Methylococcus capsulatus (CRL M1, NRRL B-11,219) were obtained by the method of Example 1. The crude extract after 10,000×g. centrifugation of sonically disrupted (3×50 sec., Wave Energy Ultrasonic Oscillator, Model W 201) was found to have no activity for either epoxidation or hydroxylation. However, when the cells were disrupted by passing twice through a French pressure cell (1000 Kg. pressure), both activities were found in the crude extract after 10,000×g. centrifugation. All of the activity in the crude extract was collected as a particulate fraction by further centrifugation of the crude extract at 40,000×g. for 90 min. at 4° C. NADH stimulated both the epoxidation and the hydroxylation reactions as shown in Table X.

TABLE X
EPOXIDATION AND HYDROXYLATION ACTIVITIES IN CELL-FREE FRACTIONS OF METHYLOCOCCUS CAPSULATUS (CRL M1, NRRL B-11,219)[a]

| Cell-Free Fractions | Oxidation Rate ($\mu$moles/30 min/assay) | |
|---|---|---|
| | Epoxidation of Propylene | Hydroxylation of Methane |
| (1) Particulate fraction (10,000 g.–40,000 g.) | 750 | 500 |
| (1) + NADH | 900 | 650 |

TABLE X-continued
EPOXIDATION AND HYDROXYLATION ACTIVITIES IN CELL-FREE FRACTIONS OF *METHYLOCOCCUS CAPSULATUS* (CRL M1, NRRL B-11,219)[a]

| | Oxidation Rate (μmoles/30 min/assay) | |
|---|---|---|
| Cell-Free Fractions | Epoxidation of Propylene | Hydroxylation of Methane |
| (2) Supernatant fraction of 40,000 g. | 0 | 0 |
| (2) + NADH | 0 | 0 |

[a]The cells were disrupted by French Press as described above. NADH (2.5 μmoles) was added into the reaction mixture where indicated. The amount of protein in the particulate fraction and the 40,000 × g. supernatant fraction used was 1 mg. and 2.5 mg., respectively. Each assay contained 0.5 ml. reaction mixture.

SUMMARY

Both the system of *Pseudomonas aeruginosa* demonstrated by Van der Linden, *Biochim. Biophys. Acta.*, 77: 157–159 (1963) and the system of *Pseudomonas oleovorans*, Abbott and Hou, *Appl. Microbiol.*, 26: 86–91 (1973) epoxidized liquid 1-alkenes from $C_6$ to $C_{12}$, but not gaseous alkenes.

The present invention provides for the epoxidation of ethylene, propylene, 1-butene and butadiene by cell suspensions of all three distinct groups of methane-utilizing bacteria. The epoxidation of alkenes and the hydroxylation of methane were not found under anaerobic conditions or in methanol-grown cells, suggesting that the enzyme system is inducible. The product 1,2-epoxides accumulated extracellularly. The non-enzymic degradation of propylene oxide in the assay system disclosed was not significant even after a prolonged incubation time. Van der Linden, supra, demonstrated the production of 1,2-epoxyoctane from 1-octene by heptane-grown cells of Pseudomonas sp. and also stated that the epxoide was not further oxidized enzymatically. However, May and Abbott, *Biochem. Biophys. Res. Commun.*, 48: 1230–1234 (1972) and *J. Biol. Chem.*, 248: 1725–1730 (1973) reported that when 1-octene was supplied as a substrate to the ω-hydroxylation enzyme system of *P. oleovorans*, both 8-hydroxy-1-octene and 1,2-epoxyoctane were formed. In addition, Abbott and Hou, supra, found that the methyl group of the latter compound was also susceptible to hydroxylation. The present results obtained from the studies of viable cell suspensions of the methane-utilizing bacteria, however, indicated that propylene oxide was not further metabolized enzymatically.

Van der Linden, supra, showed that the epxoide accumulation from 1-octene by *Pseudomonas aeruginosa* was accompanied by the metabolism of a large quantity of 1-octene via methyl group epoxidation. In the epoxidation of propylene by cell suspensions of methane-utilizing bacteria, however, no formation of 3-hydroxy propene-1 was detected.

Both the epoxidation of the $C_2$–$C_4$ 1-alkenes and the hydroxylation of methane with the cell suspensions were inhibited by various metal-binding and metal-chelating agents, indicating the involvement of metal(s)-containing enzyme system(s). The similar extent of inhibition for both propylene and methane oxidation (Table VIa) indicated that the epoxidation and hydroxylation reaction may be catalyzed by the same or a similar enzyme system. The epoxidation of propylene to propylene oxide by a cell suspension of methane-grown strain *Methylococcus capsulatus* NRRL B-11,219 was inhibited (50%) in the presence of the hydroxylation substrate, methane (Table X). This clearly suggests a competition between the hydroxylation substrate and the epoxidation substrate for a single enzyme system. It is likely that the methane mono-oxygenase enzyme system catalyzes both the epoxidation of alkene and the hydroxylation of methane. May and Abbott publications, supra, have reported that the ω-hydroxylation system from *Pseudomonas oleovorans* catalyzed both the epoxidation of 1-octene and the hydroxylation of n-octane.

The optimum conditions for the in vivo epoxidation of propylene by cell suspensions of the three distinct groups of methane-utilizing bacteria are quite similar. The pH optima were around 6–7 and the temperature optimum was around 35° C. The apparent decrease in epoxidation above 40° C. may be due to both the instability of the mono-oxygenase system and the volatility of the product propylene oxide (b.p. 35° C.).

Both the hydroxylation and epoxidation activities are located in the cell-free particulate fraction precipitated between 10,000×g. and 80,000×g. centrifugation. Tonge et al., *Biochem. J.*, 161: 333–344 (1977) and *FEBS Lett.*, 58: 293–299 (1975) have reported the purification of a membrane-bound methane mono-oxygenase from the particulate fraction (sedimented between 10,000×g. and 150,000×g. centrifugation) of *Methylosinus trichosporium* OB3b. Recently, but subsequent to our discoveries Colby et al., *Biochem. J.*, 165: 395–402 (1977) demonstrated a unique soluble methane mono-oxygenase from *Methylococcus capsulatus* (Bath strain) which catalyzes the oxidation of n-alkanes, n-alkenes, ethers and alicyclic, aromatic and heterocyclic compounds. The strains from the three distinct groups of methane-utilizing bacteria that we have examined all catalyze the epoxidation of gaseous alkenes ($C_2$–$C_4$) and the hydroxylation of gaseous alkanes ($C_1$–$C_4$). Also, we unexpectedly found the enzyme activity is in the particulate fraction (i.e., the material which sediments when the supernatant after centrifuging broken cells at 10,000×g. for 30 minutes is centrifuged for 1 hour at 10,000×g. or greater), not the soluble fraction (i.e., the supernatant after centrifuging broken cells at 80,000×g. or greater for 1 hr).

Differential centrifugation of broken-cell suspensions of Methylomonas sp. (CRL-17, NRRL B-11,208) and *Methylococcus capsulatus* (Texas ATCC 19,069), (Type I obligate methylotrophs); Methylosinus sp. (CRL-15, NRRL B-11,202) and *Methylosinus trichosporium (OB3b*, NRRL B-11,196) (Type II obligate methylotrophs); and Methylobacterium sp. CRL-16, NRRL B-11,222) (a facultative methylotroph) has yielded cell-free particulate fractions that catalyzed the hydroxylation of n-alkanes and the epoxidation of n-alkenes. Both activities mainly resided in the P(40) fraction and were dependent upon the presence of oxygen, as well as electron carrier, e.g., NADH.

The hydroxylation of methane to methanol and the epoxidation of propylene to propylene oxide catalyzed by the P(40) particulate fraction of Methylosinus sp. (CRL-15, NRRL B-11,202) have similar pH and temperature optima (FIGS. 3 & 4). Both activities were lost simultaneously during storage of the P(40) particulate fraction at refrigerator temperature.

The hydroxylation of methane and the epoxidation of propylene with the cell-free extracts were strongly inhibited by various metal-binding or metal-chelating agents (Table VI). The rate of both reactions were increased 2 fold in the presence of copper or iron salts (Table VII). This suggests the involvement of a metal-containing enzyme system in the oxidation of both substrate. These results, and the stoichiometry of the hydroxylation and the epoxidation reactions, indicate that both reactions may be catalyzed by the same metal-containing mono-oxygenase system. The fact that conversion of propylene to propylene oxide was inhibited by methane supports this proposition.

It has been reported that the cell-free particulate fractions derived from *Methylococcus capsulatus* (Texas) (Ribbons et al., *J. Bacteriol.*, 122: 1351-1363 (1975)), *Methylomonas methanica* (Ferenci et al., *J. Gen. Microbiol.* 91: 79-91 (1975)) and *Methylosinus trichosporium* (OB3b) (Tonge et al., *Biochem. J.*, 161: 333-344 ((1977)) catalyzed oxygen- and NADH-dependent oxidation of methane, ethane, propane, butane, and carbon monoxide. The oxidation of methane by particulate fractions of these organisms was inhibited by various metal-binding or metal-chelating agents. However, epoxidation of n-alkenes was not reported for these organisms.

The methane mono-oxygenase from *Methylosinus trichosporium* (OB3b, NRRL B-11,196) has been purified and shown to be consisting of three components: a soluble CO-binding cytochrome c, a copper-containing protein (methane mono-oxygenase), and a small molecular weight protein (Tonge et al., 1977, supra).

In contrast to the above organisms, Colby et al., supra have reported the unique soluble methane mono-oxygenase activity from *Methylococcus capsulatus* (Bath). The oxidation of methane by the soluble fraction of this organism was not inhibited by various metal-binding agents. Recently, Colby and Dalton (*Biochem. J.*, 171: 461-468 (1978)) resolved the methane mono-oxygenase of *Methylococcus capsulatus* (Bath) into three components and identified one of the components as an iron-containing flavorprotein.

The methane-oxidizing activities from the methylotrophic bacteria described above is in the particulate fraction and different from the soluble activity of *Methylococcus capsulatus* (Bath) disclosed by Colby et al.

Van der Linden (1963, supra) demonstrated the production of 1,2-epoxides from 1-octene by heptane-grown resting cells of Pseudomonas sp. Epoxides were not detected as products of alkane metabolism and were not oxidized by Pseudomonas sp. Thus, the role of epoxides in alkane metabolism is uncertain. Van der Linden postulated that the enzyme system that forms epoxides may be the same as the system that catalyzes the initial oxidation of alkanes. Cardini and Jurtshuk (*J. Biol. Chem.*, 245: 2789-2796 (1970)) found that a cell-free extract of a Corynebacterium sp. carried out the oxidation of 1-octene to epoxyoctane in addition to hydroxylation of octane to octanol. McKenna and Conn (*J. Biol. Chem.*, 245: 3883-3889 (1970)) isolated an enzyme system from *Pseudomonas oleovorans* that catalyzed the hydroxylation of n-alkanes ($C_6$-$C_{12}$) and fatty acids. Subsequently, Abbott and Hou, supra and May and Abbott, supra reported that the enzyme system from *Pseudomonas oleovorans* also catalyzed the epoxidation of 1-alkenes in addition to the hydroxylation reactions. The enzyme systems from Pseudomonas and Corynebacterium sp. catalyzed epoxidation of $C_6$-$C_{12}$ n-alkenes. Epoxidation of $C_2$-$C_5$ n-alkenes was not catalyzed by the Pseudomonas enzyme systems.

We have unexpectedly demonstrated that the three distinct groups of methane-oxidizing bacteria catalyze the hydroxylation of n-alkanes ($C_1$-$C_4$) as well as the epoxidation of n-alkenes ($C_2$-$C_4$). Furthermore, the hydroxylation and the epoxidation reactions are catalyzed by the same or a similar NADH-dependent mono-oxygenase.

In addition to methylotrophic bacteria, other microorganisms can be used to carry out the expoxidation of $C_2$-$C_4$ alkenes. These include bacteria, fungi and yeast which grow on short chain alkanes. The methylotrophic bacteria (obligate or facultative) or the other microorganisms are grown either on methane as a sole source of carbon, or on another carbon compound (in the presence of methane or another inducer), and the cells, or enzymes derived therefrom, may be used in the process of the present invention.

The above examples demonstrate that the three distinct groups of methane-oxidizing bacteria catalyze the hydroxylation of $C_1$-$C_4$ n-alkanes as well as the epoxidation of $C_2$-$C_4$ α-olefins and $C_4$ dienes. This enzyme system is also capable of oxidizing a plurality of related branched chain compounds and vinyl aromatic compounds. For example, the following oxidative conversions are catalyzed by the monooxygenase enzyme system: isobutene to 1,2-epoxyisobutene; isoprene to 1,2-epoxyisoprene; 2-methyl-1-butene to 2-methyl-1, 2-epoxybutane; isobutane to isobutyraldehyde and tertiary butanol; and styrene to styrene epoxide.

The following example demonstrates the enzymatic oxidation or epoxidation process with some branched chain substrates.

EXAMPLE 2

The experimental procedure described in Example 1 was used to prepare washed cell suspensions of methane-grown microorganisms and the use of the same to oxidize or epoxidize the branched chain alkanes, alkenes and dienes. Table XI shows the conversion rates for these conversions by washed cell suspensions of *Methylococcus capsulatus* (CRL-M1, NRRL B-11,219) as described more fully in U.S. Ser. Nos. 896,476 and 24,262 which had been grown under aerobic conditions on methane by the experimental procedure of Example 1.

TABLE XI

| CONVERSION OF BRANCHED CHAIN HYDROCARBONS | | |
|---|---|---|
| Substrate | Product | Reaction Rate (μmoles/hr/mg biomass) |
| Isobutane | isobutyraldehyde | 0.072 |
|  | tertiary butanol | 0.051 |
| Isobutene | 1,2-epoxyisobutene | 0.46 |
| Isoprene | 1,2-epoxyisoprene | 0.064 |
| 2,2-dimethylpropane | 2,2-dimethylpropanol | 0.085 |
| 2-methyl-1-butene | 2-methyl-1,2-epoxybutane | 0.128 |

(a)products identified by gas chromatographic retention time comparisons with authentic standards.

Isobutylene was converted to isobutylene oxide by the same procedure except that washed cell suspensions of *Methylosinus trichosporium* (OB3b, NRRL B-11,196), *Methylocooccus capsulatus* (Texas, NRRL B-11,201), Methylobacterium sp. (CRL 26 $R_6$, NRRL B-11,222) and Methylosinus sp. (CRL 15 PMI, NRRL B-11,202) were used to obtain 480, 40, 140 and 550 nmoles of isobutylene oxide per hr/mg protein, respectively. All of these conversions had an optimum pH and temperature of about 7.0 and 30° C., respectively, and the products accumulated extracellularly. In batch experiments the reactions proceeded linearly for up to 2 hours.

In Table X, it is shown that NADH stimulated both the epoxidation and the hydroxylation reactions using the monooxygenase enzyme system. These experiments show that the monooxygenase enzyme requires electron donors such as reduced nicotinamide adenine dinucleotide ($NADH_2$) or $NADPH_2$ for reducing power to catalyze the reaction. The epoxidation reaction can also be stimulated by supplying various methane metabolites, e.g., alkanes, alcohols, aldehydes, organic acids, methyl group donating compounds such as methanol, formaldehyde, formic acid, methylformate, methylcarbonate, methylacetate, methylbutyrate, dimethylether, methylamine, bromomethane, chloromethane, bromomethanol, chloromethanol, etc. where substitution in $C_1$-compound occurred by bromine, chlorine or nitro group. The following tables illustrate the stimulation effect for various C-1 methyl group donating compounds.

TABLE XII

Stimulation of Epoxidation of Propylene in Whole Cell Suspensions of Methylotrophs by Methane Metabolites

| Microbes and Metabolites Added | Epoxidation Rate (Propylene Oxide $\mu$moles/0.5 ml Assay*) | | |
|---|---|---|---|
| | 1 Hr | 2 Hr | 3 Hr |
| *Methylococcus capsulatus* CRL M1 (NRRL B-11,219) | | | |
| Control | 2.0 | 3.8 | 3.9 |
| +$CH_3OH$ (6 mM) | 2.7 | 4.2 | 5.2 |
| +$CH_3OH$ (48 mM) | 1.8 | 4.2 | 5.2 |
| +HCHO (0.25 mM) | 2.3 | 3.6 | 4.5 |
| +HCHO (4 mM) | 1.9 | 3.5 | 3.6 |
| +HCHO (10 mM) | 1.8 | 3.0 | 3.5 |
| +HCOOH (10 mM) | 2.6 | 3.7 | 4.5 |
| +HCOOH (40 mM) | 2.1 | 3.3 | 4.1 |
| *Methylosinus trichosporium* OB3b (NRRL B-11,196) | | | |
| Control | 2.1 | 3.2 | 3.3 |
| +$CH_3OH$ (6 mM) | 2.8 | 4.0 | 5.1 |
| +$CH_3OH$ (48 mM) | 1.9 | 3.8 | 5.0 |
| +HCHO (0.25 mM) | 2.4 | 3.4 | 3.9 |
| +HCHO (4 mM) | 2.0 | 3.0 | 3.1 |
| +HCHO (10 mM) | 1.8 | 2.4 | 2.5 |
| +HCHO (50 mM) | 0.8 | 1.2 | 1.3 |
| +HCOOH (10 mM) | 2.7 | 3.8 | 4.2 |
| +HCOOH (40 mM) | 2.1 | 3.3 | 4.1 |
| *Methylobacterium organophilum* CRL 26 (NRRL B-11,222) | | | |
| Control | 1.4 | 2.2 | 2.6 |
| +$CH_3OH$ (6 mM) | 1.8 | 2.5 | 3.2 |
| +$CH_3OH$ (48 mM) | 1.3 | 2.5 | 3.3 |
| +HCHO (0.25 mM) | 1.6 | 2.5 | 3.0 |
| +HCHO (4 mM) | 1.2 | 2.0 | 2.1 |
| +HCHO (10 mM) | 1.2 | 1.9 | 2.0 |
| +HCOOH (10 mM) | 1.8 | 2.6 | 3.2 |
| +HCOOH (40 mM) | 1.3 | 2.4 | 3.2 |

*Protein contents of each assay were: 0.74 mg (strain CRL), 1.1 mg (strain OB3b), and 1 mg (strain CRL 26).

As shown in Table XII, the epoxidaton of propylene to propylene oxide was stimulated by exogeneously supplying methanol, formaldehyde, or formate in all three methylotrophs tested. This stimulation could be seen during the three-hour incubaton period. The addition of methanol or formate stimulated the reaction rate. No inhibition was observed at higher concentrations (40 mM for formate and 48 mM for methanol). Exogeneously added formaldehyde, however, inhibited the epoxidation at a concentration higher than 4 mM in all the strains tested. This is contrary to the previous report by others (Stirling et al., *FEMS Microbial Letters,* 5, 315-318 (1979)) that formaldehyde (at 4 mM) stimulated the epoxidation of propylene by 3-4 times by an in vivo methane mono-oxygenase system of the Bath strain. The data in Table XII shows that there is no difference among different types of methylotrophs as to the in vivo epoxidation of propylene. Tests using ethylene as a substrate have shown that ethylene was epoxidized in vivo at the same magnitude by these methylotrophs without an exogenous supply of reducing power. The addition of methane metabolites also stimulated the epoxidation of ethylene. Interestingly, these methane metabolites failed to stimulate the in vivo hydroxylation of n-alkanes.

Therefore, the results shown above suggest that the oxidation of alkanes, alcohols (primary, secondary, tertiary alcohols), aldehydes or organic acids by cell-suspensions of organisms will generate the necessary reducing power ($NADH_2$ or $NADPH_2$) required for the epoxidaton of alkenes, dienes or vinyl aromatic compounds. As discussed above the enzyme (monooxygenase) which catalyzes the epoxidation reaction requires an electron carrier or cofactor, NADH, for its activity. When the cofactor is depleted, it can be regenerated by the addition of compounds which are substrates for dehydrogenases or oxidases such as alcohol (primary and/or secondary) dehydrogenase, aldehyde dehydrogenase, formate dehydrogenase, steroid dehydrogenase, etc. in either cell-free or whole cell systems. The overall catalyst system is stabilized by coupling this cofactor regeneration system to the epoxidation reaction process.

A schematic explanation of the coupling cycle for the regeneration of cofactor is shown below:

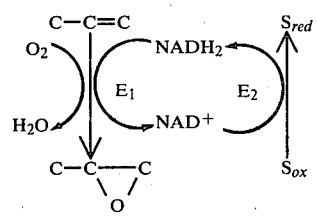

wherein $E_1$ is the monooxygenase enzyme, $E_2$ is the dehydrogenase enzyme and S is the substrate for cofactor regeneration.

The following summarizing comments can be based on the above.

(1) Cofactor regeneration through methanol dehydrogenase.

All of the $C_1$-utilizing microbes possess methanol dehydrogenase activity. When methanol was added into the propylene epoxidation or propane hydroxylation system, the yield of propylene oxide or acetone as well as the life time of the biocatalyst were improved. Some inhibition were observed at higher methanol concentration (>24 $\mu$moles) within the first hour of reaction. Since methanol dehydrogenase is a non-specific primary alcohol dehydrogenase, other alcohols could also be used.

(2) Cofactor regeneration through aldehyde dehydrogenase.

All of the $C_1$-utilizing microbes possess formaldehyde dehydrogenase. Therefore, formaldehyde was added into the propylene epoxidation or propane hydroxylation system. Formaldehyde at lower concentration (0.125 $\mu$moles/015 ml) stimulated both the epoxidation of propylene and the hydroxylation of propane. Other aldehydes could replace formaldehyde for the regeneration of NADH. However, formaldehyde at higher than 2.0 μmoles/0.5 ml inhibited both reactions.

(3) Cofactor regeneration through formate dehydrogenase.

$C_1$-utilizing microbes possess formate dehydrogenase. Therefore, formate was added into the propylene epoxidation or propane hydroxylation system. We have shown above that both reactions and the life time of the biocatalyst were improved. Delayed addition of formate (after one hour of reaction i.e. after most of the endogeneous NADH was consumed) greatly stimulated the epoxidation of propylene.

(4) Cofactor regeneration through secondary alcohol dehydrogenase (SADH).

SADH which oxidized secondary alcohols to methyl ketones catalyzed simultaneously the reduction of $NAD^+$ to NADH. All of the $C_1$ to $C_4$-utilizing microbes have SADH activity. Therefore, 2-butanol was added into the epoxidation system (biocatalyst from $C_1$-$C_4$ gaseous alkane-grown microbes). Results we have obtained indicate that the epoxidation of gaseous n-alkenes is somehow inhibited. However, the products obtained here were propylene oxide, methyl ethyl ketone and 2,4-butanediol.

In Tables VIII and VIIIa it was shown that methane competes with propylene for the mono-oxygenase enzyme when the experiments were assayed at 30 minutes with a large amount of methane. It is known that methylotrophic bacteria utilize methane as their sole source of carbon and energy. In other words, methane as electron donor supplies energy or generates reducing power which can be used for monooxygenase activity. The following experiments were conducted using a stimulating (non-competing) amount of methane to stimulate production of propylene oxide. The oxygen content of the gaseous phase was ketp constant (50%) in all the experiments. In the experiments it was found that the supply of methane at a stimulating level of methane improved both the epoxidation of propylene and the lifetime of the biocatalyst. The following table, using a washed cell suspension of methane grown *Methylococcus capsulatus* CRL M1 (NRRL B-11,219), shows the expoxidation rates for propylene oxide formation using methane as a stimulator at levels ranging from 5 to 20 volume %.

TABLE XIII

STIMULATION OF EPOXIDATION WITH METHANE

| Substrate | Epoxidation Rate Propylene oxide, μmoles/0.5 ml | | |
|---|---|---|---|
|  | 1 Hr | 2 Hr | 3 Hr |
| Propylene (control) | 2.0 | 3.8 | 3.9 |
| Propylene + 5% methane | 2.0 | 4.0 | 4.1 |
| Propylene + 7% methane | 2.3 | 4.7 | 4.8 |
| Propylene + 15% methane | 3.5 | 6.4 | 6.5 |
| Propylene + 20% methane | 3.8 | 7.1 | 7.2 |

As shown in Table XIII, when a stimulating amount of methane, i.e. from about 5 to about 20 volume % methane, is utilized the epoxidation rate and life of the enzyme are increased. Thus, the addition of methane will stimulate the reaction as long as the level is less than an equivalent amount compared to the olefin.

It will be understood that initially, the methane competes with the olefin for the enzyme. However, as the methane is oxidized to methanol, the methanol thus produced stimulates the reaction.

Several experiments were carried out using a plurality of compounds capable of generating the necessary reducing power ($NADH_2$ or $NADPH_2$) required for the epoxidation of alkenes or dienes. These experiments were carried out using cell suspensions of methane grown methylotrophs using the procedure as described in Example 1 except that a stimulator compound was added to the reaction medium. The results are shown in Tables XIV, XV, and XVI.

TABLE XIV

STIMULATION OF EPOXIDATION REACTION IN *METHYLOBACTER CAPSULATUS* STRAIN Y[b]
IN THE PRESENCE OF C-1 COMPOUNDS, METHYL GROUP DONATING COMPOUNDS, ALCOHOLS AND ALDEHYDES

| Substrate | Product | Rate of Product Formation[a] nmoles/hr/ mg protein |
|---|---|---|
| Propylene | Propylene Oxide | 2 |
| Propylene + 5 mM Methanol | Propylene Oxide | 79 |
| Propylene + 5 mM Methyl Formate | Propylene Oxide | 99 |
| Propylene + 5 mM Ethanol | Propylene Oxide | 370 |
| Propylene + 5 mM Propionaldehyde | Propylene Oxide | 54 |
| Propylene + 5 mM Isopropanol | Propylene Oxide | 13 |
| Propylene + 5 mM 2-Butanol | Propylene Oxide | 26 |

[a] The product of epoxidation reaction was identified and estimated by gas chromatography retention time comparison and co-chromatography with authentic standard.
[b] NRRL B-11,201

TABLE XV

STIMULATION OF EPOXIDATION REACTION IN *METHYLOCOCCUS CAPSULATUS* STRAIN MC[b]
IN THE PRESENCE OF C-1 COMPOUNDS, METHYL GROUP DONATING COMPOUNDS, ALCOHOLS, AND ALDEHYDES

| Substrate | Product | Rate of Product Formation[a] nmoles/hr/ mg protein |
|---|---|---|
| Propylene | Propylene Oxide | 3.5 |
| Propylene + 5 mM Methanol | Propylene Oxide | 554 |
| Propylene + 5 mM Methyl Formate | Propylene Oxide | 390 |
| Propylene + 5 mM Ethanol | Propylene Oxide | 462 |
| Propylene + 5 mM Propanol | Propylene Oxide | 243 |
| Propylene + 5 mM Acetaldehyde | Propylene Oxide | 154 |
| Propylene + 5 mM Propionaldehyde | Propylene Oxide | 40 |
| Propylene + 5 mM Acetate Methyl | Propylene Oxide | 21 |
| Propylene + 5 mM 2-Propanol | Propylene Oxide | 37 |
| Propylene + 5 mM 2-Butanol | Propylene Oxide | 21 |

[a] The product of epoxidation reaction was identified and estimated by gas chromatography retention time comparison and co-chromatography with authentic standard.
[b] Known strain from Whittenbury.

TABLE XVI
STIMULATION OF EPOXIDATION REACTION IN
*METHYLOBACTERIUM ORGANOPHILUM* R6[b]
IN THE PRESENCE OF C-1 COMPOUNDS,
METHYL GROUP DONATING COMPOUNDS,
ALCOHOLS, AND ALDEHYDES

| Substrate | | Product | Rate of Product Formation[a] nmoles/hr/ mg protein |
|---|---|---|---|
| Propylene | | Propylene Oxide | 10 |
| Propylene + | 5 mM Methanol | Propylene Oxide | 101 |
| Propylene + | 5 mM Ethanol | Propylene Oxide | 124 |
| Propylene + | 5 mM Dimethylether | Propylene Oxide | 50 |
| Propylene + | 5 mM Methyl Formate | Propylene Oxide | 61 |
| Propylene + | 5 mM Acetaldehyde | Propylene Oxide | 13 |
| Propylene + | 5 mM Methyl Acetate | Propylene Oxide | 5.0 |
| Propylene + | 5 mM Propanol | Propylene Oxide | 66 |
| Propylene + | 5 mM Isopropanol | Propylene Oxide | 20 |

[a] The product of epoxidation reaction was identified and estimated by gas chromatography retention time comparison and co-chromatography with authentic standard.
[b] NRRL B-11,222

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process of epoxidation of a $C_2$-$C_4$ alpha-olefin, a $C_4$-$C_5$ branched olefin, a $C_4$-$C_5$ diene or a vinyl aromatic compound in a reaction medium which comprises: epoxidizing said olefin, diene or vinyl aromatic compound by contacting said olefin, diene or vinyl aromatic compound under aerobic conditions in the presence of cells of a bacterial methylotrophic microorganism, a genetically engineered derivative of said cells, or an oxygenase enzyme preparation prepared from said cells or a genetically engineered derivative thereof, wherein said cells, derivative or enzyme preparation exhibit epoxidase enzyme activity, until at least an isolatable amount of the corresponding epoxide is obtained, wherein said microorganism has been aerobically grown in a nutrient medium containing methane.

2. The process of claim 1 wherein the enzyme preparation is derived from a cell-free extract of the microorganisms.

3. The process of claims 1 or 2 wherein an electron carrier is added to said reaction medium.

4. The process of claim 3 wherein NADH is the electron carrier.

5. The process of claim 4 wherein a metal is added to said reaction medium which enhances the enzymes' activity.

6. The process of claim 3 wherein the electron carrier required to drive the enzymatic reaction is regenerated.

7. The process of claims 1 or 2 wherein an electron donor is added to the reaction medium.

8. The process of claim 7 wherein the electron donor is produced from methane, methane metabolites, or methyl group donating compounds.

9. The process of claim 7 wherein the electron donor is selected from the group consisting of methane, methanol, formaldehyde, formic acid, methylformate, methyl carbonate, methyl acetate, methyl butyrate, dimethylether, methylamine, bromomethane, chloromethane, bromomethanol, isopropanol, 2-butanol, acetaldehyde and propionaldehyde.

10. A process for the epoxidation of propylene in a reaction medium which comprises: epoxidizing propylene by contacting propylene under aerobic conditions in the presence of cells of a bacterial methylotrophic microorganism, a genetically engineered derivative thereof, or a monooxygenase enzyme preparation prepared from said cells or a genetically engineered derivative thereof, wherein said cells, derivative or enzyme preparation exhibit epoxidase enzyme activity, until at least an isolatable amount of propylene oxide is obtained, wherein said microorganism has been aerobically grown in a nutrient medium containing methane.

11. The process of claim 10 wherein said microorganisms are obligate or facultative methylotrophs.

12. The process of claim 11 wherein said microorganisms belong to the genera selected from the group consisting of Methylosinus, Methylocystis, Methylomonas, Methylobacter, Methylococcus and Methylobacterium.

13. The process of claim 11 wherein said microorganisms are species selected from the group consisting of: *Methylosinus trichosporium, Methylosinus sporium, Methylocystis parvus, Methylomonas methanica, Methylomonas albus, Methylomonas streptobacterium, Methylomonas agile, Methylomonas rubrum, Methylomonas rosaceus, Methylobacter chroococcum, Methylobacter bovis, Methylobacter capsulatus, Methylobacter vinelandii, Methylococcus capsulatus, Methylococcus minimus* and *Methylobacterium organophilum*.

14. The process of claim 11 wherein said microorganisms are strains selected from the group consisting of: *Methylosinus trichosporium* OB3b (NRRL B-11,196); *Methylosinus sporium* 5 (NRRL B-11,197); *Methylocystis parvus* OBBP (NRRL B-11,198); *Methylomonas methanica* $S_1$ (NRRL B-11,199); *Methylomonas albus* BG 8 (NRRL B-11,200); *Methylobacter capsulatus* Y (NRRL B-11,201); *Methylobacterium organophilum* sp nov. (ACTT 27,886); Methylomonas sp AJ-3670 (FERM P-2400); Methylococcus 999 (NCIB Accession No. 11,083); and Methylomonas SM3 (NCIB Accession No. 11,084).

15. The process of claim 10 wherein the epoxidation is carried out at a temperature in the range from about 5° to about 55° C. at a pH in the range from about 4 to about 9.

16. The process of claim 10 wherein the epoxidation is carried out at a temperature in the range from about 25° to about 50° C. and at a pH in the range from 5.5 to 7.5.

17. The process of claim 10 wherein oxygen is used in the form of air.

18. The process of claim 10 wherein the epoxidation is carried out batchwise.

19. The process of claim 10 wherein the epoxidation is carried out in a batchwise manner and the enzyme preparation is immobilized.

20. The process of claim 10 wherein the epoxidation is carried out in a continuous manner and the enzyme preparation is immobilized.

21. The process of claims 10 or 20 wherein an electron carrier is added.

22. The process of claim 21 wherein NADH is the electron carrier.

23. A process according to claim 22 wherein said methylotroph belongs to the genus Methylosinus.

24. A process according to claim 22 wherein said methylotroph belongs to the species *Methylosinus trichosporium*.

25. A process according to claim 22 wherein the methylotroph is *Methylosinus trichosporium* OB3b.

26. A process according to claims 23, 24, or 25 wherein a compound containing one carbon atom is present as an electron donor.

27. A process according to claims 23, 24, or 25 wherein methane or methanol is added as an electron donor.

28. The process of claims 10 or 20 wherein a stimulating amount of an electron donor produced from methane, a methane metabolite or a methyl group donating compound is added to the reaction medium.

29. The process of claim 21 wherein the electron carrier required to drive the enzymatic reaction is regenerated.

30. A process for the epoxidation of propylene in a reaction medium which comprises the sequential steps of:
   (a) incubating, under aerobic conditions, a nutrient medium containing methane and a bacterial obligate or facultative methylotrophic microorganism or a genetically engineered derivative thereof to produce a monooxygenase enzyme system having epoxidase activity, and
   (b) epoxidizing propylene by contacting propylene, under aerobic conditions, with said monooxygenase enzyme system, until at least an isolatable amount of propylene oxide is obtained.

31. The process of claim 30 wherein said microorganisms belong to the genera selected from the group consisting of Methylosinus, Methylocystis, Methylomonas, Methylobacter, Methylococcus, and Methylobacterium.

32. The process of claim 30 wherein said microorganisms belong to the genera selected from the group consisting of *Methylosinus trichosporium, Methylosinus sporium, Methylocystic parvus, Methylomonas methanica, Methylomonas albus, Methylomonas streptobacterium, Methylomonas agile, Methylomonas rubrum, Methylonomas rosaceus, Methylobacter chroococcum, Methylobacter bovis, Methylobacter capsulatus, Methylobacter vinelandii, Methylococcus capsulatus, Methylococcus minimus* and *Methylobacterium organophilum*.

33. The process of claim 30 wherein said microorganisms are strains selected from the group consisting of: *Methylosinus trichosporium* OB3b (NRRL B-11,196); *Methylosinus sporium* 5 (NNRL B-11,197); *Methylocystic parvus* OBBP (NRRL B-11,198); *Methylomonas methanica* $S_1$ (NRRL B-11,199); *Methylomonas albus* BG 8 (NRRL B-11,200); *Methylobacter capsulatus* (NRRL B-11,201); *Methylobacterium organophilum* sp nov (ATCC 27,886); Methylomonas sp AJ-3670 (FERM P-2400); Methylococcus 999 (NCIB Accession No. 11083); and Methylomonas SM3 (NCIB Accession No. 11084).

34. The process of claim 30 wherein the cultivation in step (a) and the epoxidation in step (b) are carried out at a temperature in the range from about 25° to about 50° C. and at a pH in the range from about 5.5 to 7.5

35. The process of claim 30 wherein steps (a) and (b) are carried out in a continuous manner.

36. The process of claims 1, 10 or 30 wherein an electron carrier and a stimulating amount of an electron donor are present in the reaction medium.

37. The process of claim 36 wherein a dehydrogenase enzyme is included in the reaction medium.

38. The process of claim 37 wherein the dehydrogenase enzyme is selected from the group consisting of aldehyde dehydrogenase, formate dehydrogenase and steroid dehydrogenase.

39. The process of claim 37 wherein the dehydrogenase enzyme is a secondary alcohol dehydrogenase enzyme.

40. The process of claim 36 wherein the electron carrier is selected from the group consisting of NAD or $NADH_2$.

41. The process of claim 36 wherein the electron donor is methane, a methane metabolite or a methyl group donating compound.

42. A process of epoxidation of $C_2$–$C_4$ n-alkenes, $C_4$–$C_5$ branched alkenes, $C_4$–$C_5$ dienes or vinyl aromatic compounds which comprises epoxidizing a $C_2$–$C_4$ n-alkene, a $C_4$–$C_5$ branched alkene, a $C_4$–$C_5$ diene or a vinyl aromatic compound using a culture of methane-utilizing bacterial methylotrophs or an extract thereof containing a monooxygenase enzyme system exhibiting epoxidase enzyme activity as an epoxidizing agent, until at least an isolatable amount of the corresponding epoxide is obtained.

* * * * *